US00PP11550P

United States Patent [19]

Jonkers

[11] Patent Number: Plant 11,550

[45] Date of Patent: Oct. 3, 2000

[54] IMPATIENS PLANT NAMED 'DIDI SCARLET'

[75] Inventor: J. B. Hanneke Jonkers, Hoorn, Netherlands

[73] Assignee: Goldsmith Plants, Inc., Gilroy, Calif.

[21] Appl. No.: 09/078,644

[22] Filed: May 14, 1998

[51] Int. Cl.[7] ..... A01H 5/00

[52] U.S. Cl. ..... Plt./317

[58] Field of Search ..... Plt./317

[56] References Cited

PUBLICATIONS

GTITM UPOVROM Citation for 'Didi Scarlet' as per QZ PBR 952882; Oct. 25, 1995.

*Primary Examiner*—Howard J. Locker
*Assistant Examiner*—Kent L. Bell
*Attorney, Agent, or Firm*—Rothwell, Figg, Ernst & Manbeck

[57] ABSTRACT

A new and distinct cultivar of Impatiens plant, and named 'Didi Scarlet' is provided. 'Didi Scarlet' is distinct in its scarlet colored fully double flowers, its early and free flowering, and its basal branched, compact growth habit.

2 Drawing Sheets

BACKGROUND OF THE NEW PLANT

The present invention comprises a new and distinct cultivar of impatiens, botanically known as *Impatiens walleriana*, and hereinafter referred to by the cultivar name 'Didi Scarlet', and is characterized by the following combination of repeatedly observed traits:

1. Fully double flowers,
2. early flowering,
3. compact basal branching, and
4. free flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1791-12 (unpatented) and the male parent (i.e., pollen parent) was an *Impatiens walleriana* named IM-795-3 (unpatented). The cross was made in 1995 and the seedling was selected in 1996.

This new cultivar has been identified as Impatiens 'Didi Scarlet'. The new cultivar is being marketed under the trademark name Double Diamond Scarlet.

DESCRIPTION OF THE PHOTOGRAPHS

This new impatiens plant is illustrated by the accompanying photograpic drawings in full color, the colors shown being as true as can be reasonably obtained by conventional photographic procedures.

DESCRIPTION OF THE NEW CULTIVAR

Figure 1:
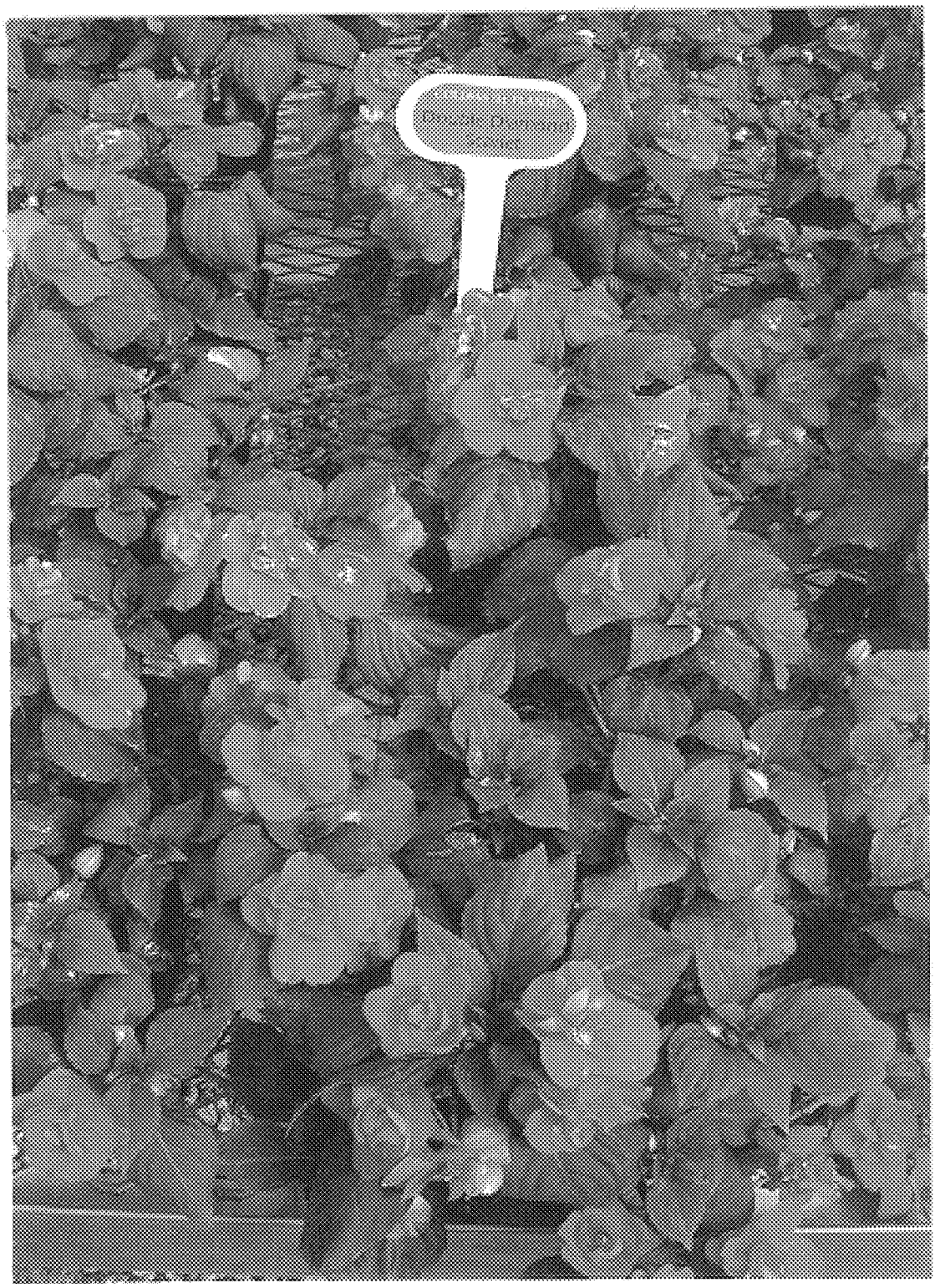
FIG. 1 shows a top perspective view of typical plants of the new cultivar.
Figure 2:
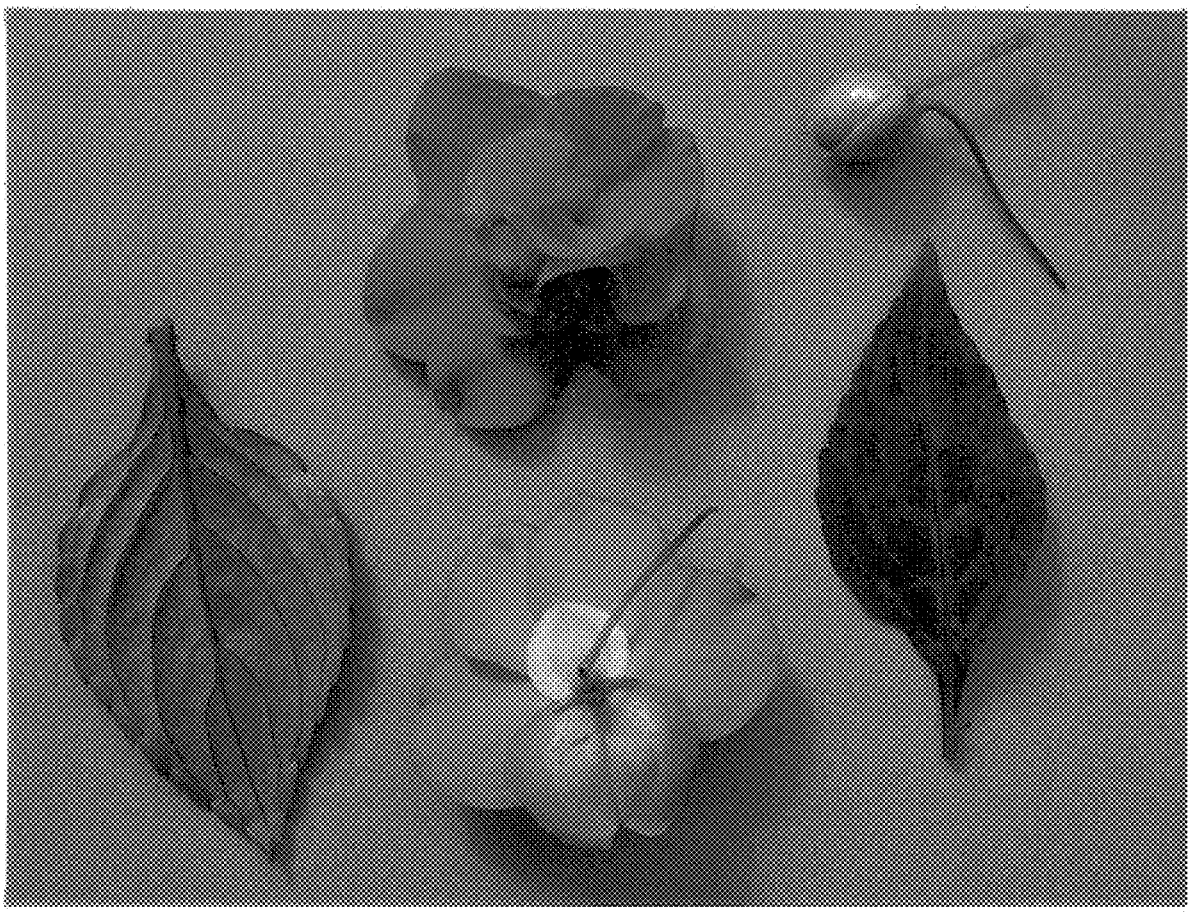
FIG. 2 shows an individual bud and the upper and lower sides of flower and foliage.

The following observations and measurements describe plants grown outside in the field in Andijk, The Netherlands. Measurements were recorded in August, 1997, on plants approximately 14 weeks old. Fully developed organs were used for measurements and color descriptions, unless otherwise indicated. Color references are made to the R.H.S. Colour Chart of The Royal Horticultural Society, London, England, except where general color terms of ordinary significance are used.

'Didi Scarlet' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* IN-1791-12 (unpatented).

*Male parent.*—*Impatiens walleriana* IM-795-3 (unpatented).

Propagation:

*Type cutting.*—Stem (internodal) cutting with two nodes and attached leaves.

*Time to initiate roots.*—10–14 days at 70–75 degrees F. with a fully developed root mass at 21 days.

*Rooting habit.*—Fibrous, branching, adventitious root system.

Plant description:

*Form.*—Upright

*Growth habit.*—Upright branching plant habit with upper leaves and flowers produced in whorls. When grown in a 4 inch pot for 10–12 weeks the height is approximately 4–5 inches and the width is approximately 5 inches.

*Foliage description.*—Leaves are simple. Lower leaf arrangement is alternate with upper leaves arranged in whorls of 5. Leaf shape is ovate with acute apex and acute base. Leaf size is 4.5 cm×3 cm. Leaf margin is crenate with ciliation. Leaf surface is glabrous. Leaf color is green. The upper surface is yelow-green group 147A. Under surface is yellow-green group 147B with greyed-purple mottling ranging from 182A to 182C through 183D. Venation is pinnate 147A for the upper surface and 147B for the lower surface.

*Petiole.*—Petiole length is 2 cm; and diameter is 0.2 cm: Color is yellow-green 147C.

Flower description:

*Flowering habit.*—Rooted cutting to full flowering plant in seven weeks. Indeterminate, flowering continuously. Flowers develop in the upper leaf axils.

*Natural flowering season.*—Flowers continuously throughout the year.

*Flowers borne.*—On pedicels which are yellow-green 145A and 3 cm long in clusters of 2–7 flowers with a peduncle color of yellow-green 145A and length of 2 cm long.

*Spur.*—Short spurred; length is 3.5 cm; color is 161B.

*Buds.*—Buds are oval-shaped at first color 39A and 145C; size is 1.3 cm×1.0 cm.

*Quantity of flowers.*—Floriferous. Each axillary cluster of 2–7 flowers developing progressively from the leaf whorls so that buds as well as mature flowers are visible at the same time in large numbers.

*Petals.*—Number of petals 18–22, with all petals overlapping. Outer petals average 2.5 cm length×2.0 cm width and inner petals average 0.7 cm length×0.5 cm width. All petals are slightly cupped.

*Flower color.*—Upper surface: Red group 45C. Lower surface: Red group 45D.

*Flower size.*—Approximately 4 cm wide and 4 cm long.

*Reproductive organs.*—No reproductive organs.

Disease and Insect Resistance

No known susceptibility to diseases or insects noted to date.

Comparison with the Known Cultivars

When 'Didi Scarlet' is compared to Impatiens 'Fiesta Salsa Red' (unpatented), it is found that 'Didi Scarlet' exhibits a more vigorous plant habit and is also more floriferous.

When 'Didi Scarlet' is compared to 'IN-1791-12' and 'IM-795-3', the parental cultivars, the instant cultivar has double flowers and the parental cultivars are both single flowering.

When 'Didi Scarlet' is compared to co-pending U.S. Plant Patent application Ser. No. 09/078,642 for Impatiens 'Didi Red', the primary difference is the color. 'Didi Red' has flower colors of R.H.S. 53C and 53D and 'Didi Scarlet' has flower colors of R.H.S. 45C and 45D.

I claim:

1. A new and distinct cultivar of Impatiens plant named 'Didi Scarlet', substantially as described and illustrated herein, characterized particularly as to novelty by its fully double scarlet colored flowers, its early and free flowering, and its basal branched, compact growth habit.

* * * * *